(12) United States Patent
Eberhardt et al.

(10) Patent No.: US 7,271,309 B2
(45) Date of Patent: Sep. 18, 2007

(54) METHOD FOR THE CATALYTICALLY REACTING OF ISOPARAFFINS WITH OLEFINS TO FORM ALKYLATES

(75) Inventors: Jürgen Eberhardt, Rodgau (DE); Walter Boll, Frankfurt am Main (DE); Henning Buchold, Hanau (DE); Holger Dropsch, Bad Vilbel (DE)

(73) Assignee: MG Technologies AG, Frankfurt am Main (DE)

( * ) Notice: Subject to any disclaimer, the term of this patent is extended or adjusted under 35 U.S.C. 154(b) by 204 days.

(21) Appl. No.: 10/477,773

(22) PCT Filed: Mar. 26, 2002

(86) PCT No.: PCT/EP02/03360

§ 371 (c)(1),
(2), (4) Date: Apr. 27, 2004

(87) PCT Pub. No.: WO02/094747

PCT Pub. Date: Nov. 28, 2002

(65) Prior Publication Data

US 2004/0242950 A1    Dec. 2, 2004

(30) Foreign Application Priority Data

May 22, 2001   (DE) ............................... 101 25 230

(51) Int. Cl.
*C07C 2/58* (2006.01)

(52) U.S. Cl. ..................................... 585/722; 585/714
(58) Field of Classification Search ............... 585/722, 585/714

See application file for complete search history.

(56) References Cited

U.S. PATENT DOCUMENTS 5,292,981 A    3/1994   Huang et al.
5,346,676 A *  9/1994   Crossland et al. .......... 422/211

* cited by examiner

*Primary Examiner*—Thuan Dinh Dang
(74) *Attorney, Agent, or Firm*—Norris McLaughlin & Marcus PA

(57) ABSTRACT

In the presence of a catalyst, at least one isoparaffin having 4 to 6 C atoms per molecule is reacted with at least one olefin having 2 to 6 C atoms per molecule in a liquid phase to obtain a product containing alkylate, a suspension containing isoparaffin and a granular zeolite catalyst being supplied to the upper region of a reaction column. Below the point where the catalyst-containing suspension is supplied, an isoparaffin-olefin mixture is introduced into the reaction column, the temperatures in the reaction column being maintained in the range from 50 to 120° C. From the bottom region of the reaction column a product mixture containing alkylate is withdrawn, and in a separation by distillation alkylate product is recovered therefrom. Preferably, isoparaffin and catalyst are recovered from the separation by distillation and at least partly recirculated to the upper region of the reaction column.

3 Claims, 1 Drawing Sheet

METHOD FOR THE CATALYTICALLY REACTING OF ISOPARAFFINS WITH OLEFINS TO FORM ALKYLATES

This is a 371 of PCT/EP02/03360 filed 26 Mar. 2002 (international filing date).

BACKGROUND OF THE INVENTION

This invention relates to a process for the catalytic reaction of at least one isoparaffin having 4 to 6 C atoms per molecule with at least one olefin having to 2 to 6 C atoms per molecule in a liquid phase to obtain a product containing alkylate.

SUMMARY OF THE INVENTION

It is the object underlying the invention to perform this process at low cost with a high yield of alkylate and a low amount of byproducts. In accordance with the invention, this is achieved in that a suspension containing isoparaffin and a granular zeolite catalyst is supplied to the upper region of a reaction column, that below the point where the catalyst-containing suspension is supplied an isoparaffin-olefin mixture is introduced into the reaction column, the temperatures in the reaction column being maintained in the range from 50 to 120° C., that from the bottom region of the reaction column a product mixture containing alkylate is withdrawn and alkylate product is recovered therefrom in a separation by distillation. Preferably, the temperatures in the reaction column lie in the range from 60 to 100° C.

For the process it is important that in the reaction column, at the point where the olefin meets with isoparaffin and the catalyst, the olefin is only present in a rather low concentration, in order to largely exclude that the olefin reacts with itself.

The reaction column has a plurality of gas- and liquid-permeable trays, and the mixture to be reacted runs downwards in the column over the trays. Expediently, a liquid mixture should be kept on at least some of the trays, and at the same time vaporous isoparaffin is passed through the mixture from below. In the reaction chamber, there is usually employed a pressure of 5 to 20 bar.

The process can be used, for instance, to catalytically react isobutane with butene to obtain isooctane and thus produce an additive for gasoline.

Suitable catalysts include X-type, Y-type or LSX-type zeolites, which are commercially available and are produced e.g. by Südchemie, Munich (Germany).

BRIEF DESCRIPTION OF THE DRAWINGS

Embodiments of the process will be explained with reference to the drawing, in which.

DETAILED DESCRIPTION

Figure 1:
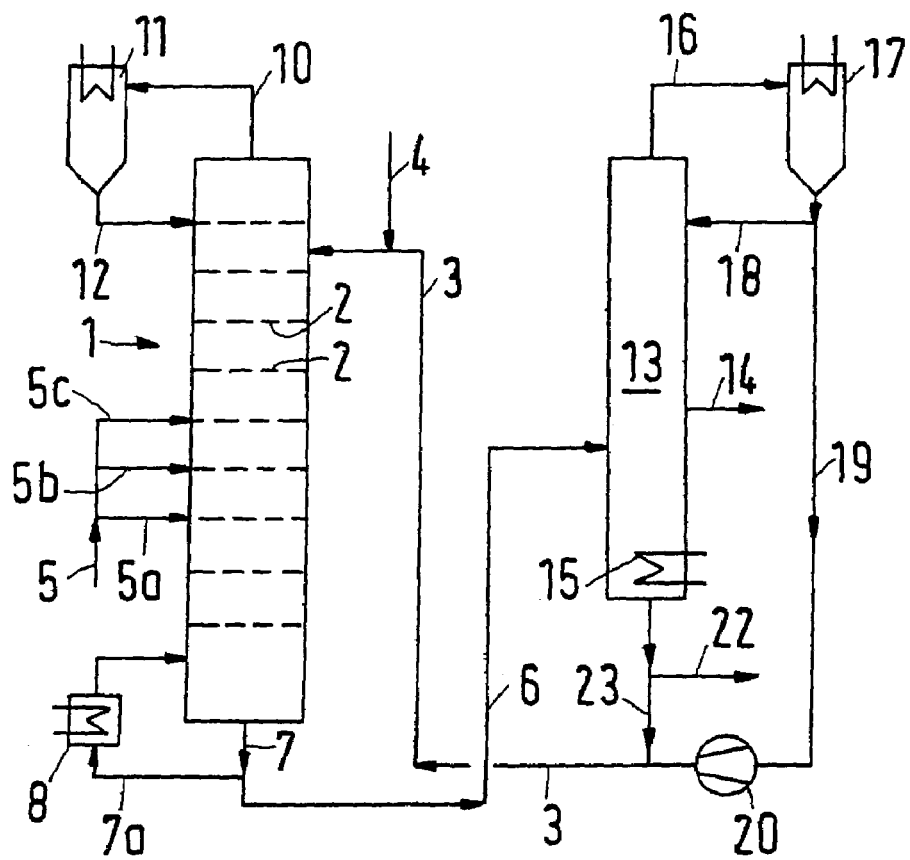
FIG. 1 shows a flow diagram of the process.

As shown in FIG. 1, the reaction takes place in a reaction column (1) which has numerous horizontal trays (2), e.g. 5 to 20 trays. The trays (2) are gas- and liquid-permeable. To the upper region of the column (1), a suspension containing isoparaffin and granular zeolite catalyst is charged through line (3), fresh catalyst being added through line (4). Via line (5), a mixture of isoparaffin and olefin is supplied, which is charged to the reactor (1) via a plurality of branch lines (5a), (5b) and (5c). Expediently, it is ensured that the isoparaffin-olefin mixture entering the reactor (1) has a relatively low olefin content in the range from 1 to 50 wt-%.

From the bottom of the reaction column (1), a product mixture containing alkylate is withdrawn via line (7), and a heated and at least partly evaporated partial stream is recirculated through line (7a) and the boiling vessel (8) to the column (1). Thereby, the temperature in the column (1) is maintained in the desired range. Vapor escaping from the top of the column (1) flows through line (10) into the condenser (11) with integrated separator, and the condensate is recirculated to the top of the column through line (12).

A partial stream of the product mixture containing alkylate flows through line (6) into a distillation column (13) from which the separated alkylate product is withdrawn through line (14). The distillation column (13) is provided with a bottom heating (15). Vapors containing isoparaffin are supplied through line (16) to a condenser (17) and accumulate in a subsequent separator, from where a partial stream is recirculated through line (18) to the top of the column (13). The rest of the condensate chiefly containing isoparaffin flows through line (19) to a pump (20) and is then combined with the partial fraction supplied via line (23). This fraction contains high-boiling components and catalyst, and part of this fraction is removed from the process through line (22). The suspension containing isoparaffin and catalyst, which has thus been formed, flows back through line (3) to the reaction column (1).

Figure 2:
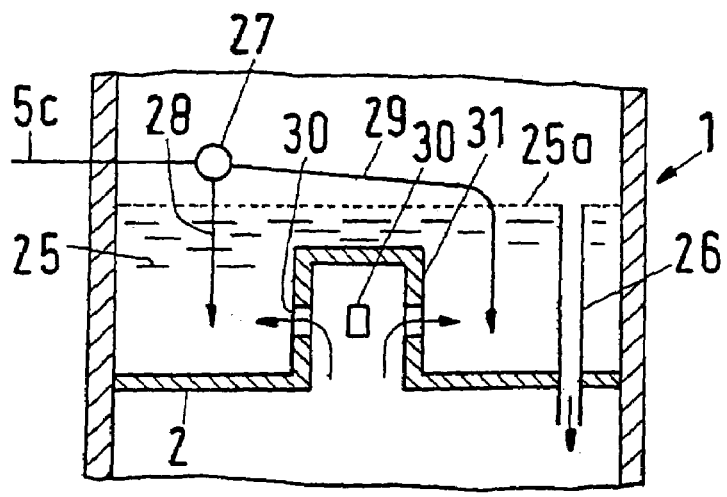
FIG. 2 shows a vertical section through a tray of the reaction column.

FIG. 2 shows a portion of the reaction column (1) with a tray (2) on which a liquid mixture (25) is kept. The liquid level (25a) indicated by a dotted line is determined by the upper inlet of a passage (26) through which the liquid flows downwards to the next tray, which is not represented here. From outside, an isoparaffin-olefin mixture is supplied through the branch line (5c) and first of all enters a distributing pipe (27), from where it flows out through a plurality of line branches (28) and (29) to the tray (2). In this way it is ensured that the olefin concentration in the liquid mixture (25) locally can only reach a low maximum.

The tray (2) of FIG. 2 has a cylindrical vapor outlet (31) closed at the top and provided with a plurality of openings (30). In reality, a plurality of these vapor outlets (31) are distributed on each tray. It thus becomes possible that vapor containing isoparaffin, which rises from below, can flow through the openings (30) into the liquid mixture (25), where it is at least partly reacted.

EXAMPLE

In a laboratory plant corresponding to the drawing, there was examined the alkylation of isobutane with 2-butene in a continuously operated reaction column (1) with ten trays as reaction apparatus. For this purpose, the reaction column was charged every hour with a suspension of 280 g solid, fine-grained zeolite catalyst (X-type zeolite of Südchemie, Munich (Germany)) in 350 g isobutane. The suspension was charged to the reaction column through line (3). Through line (5), the reaction column was furthermore charged with a feed stream of 350 g/h isobutane and 56 g/h 2-butene (ratio isobutane/butene=6 mol/mol; catalyst load=0.2 g butene $h^{-1}$ (g cat.)$^{-1}$). The isobutane surplus should prevent the reaction of the butenes with themselves (e.g. by oligomerization or polymerization). The feed stream of line (5) was charged to the reaction column distributed over 4 trays. The reaction column was operated at a pressure of 11 bar. The operation of the reaction column under boiling conditions with vapor flowing upwards ensured a good mixing of the reaction mixture with the catalyst suspension on the individual column trays. The condensate obtained in the condenser (11) is completely recirculated to the column. Under these conditions, 754 g/h liquid reaction product with a temperature of 75° C. were obtained in line (6), and the composition of this reaction product is indicated in column A of the Table below, column B indicating the amounts without the two feed materials.

|  | A (wt-%) | B (wt-%) |
|---|---|---|
| Isobutane | 84.90 | — |
| 2-butene | 0.00 | — |
| Sum of $C_5$ components | 0.65 | 4 |
| Sum of $C_6$ components | 0.73 | 5 |
| Sum of $C_7$ components | 0.82 | 6 |
| Sum of $C_8$ components | 10.90 | 72 |
| Sum of $C_9$ components | 2.00 | 13 |

The data indicated in the Table reveal that the predetermined amount of 2-butene is completely reacted to obtain $C_{5+}$ products. The selectivity for the $C_8$ hydrocarbons in the alkylate is about 72 wt-%; a high content of $C_8$ hydrocarbons in the alkylate product is advantageous for its use as motor gasoline additive.

Furthermore, the amount of catalyst added at the top of the column was received back at the bottom of the column. The mixture of reaction product and catalyst withdrawn at the bottom of the column can subsequently be supplied to a distillation, in order to separate the alkylate product from the non-reacted isobutane as well as the catalyst. The isobutane/catalyst mixture thus obtained can be recirculated to the reaction column through line (3), which was omitted in the laboratory experiments. The laboratory experiments should merely examine the technical feasibility of the process in a simple passage through the process stages described.

We claim:

1. A process for the catalytic reaction of at least one isoparaffin having 4 to 6 C atoms per molecule with at least one olefin having 2 to 6 C atoms per molecule in a liquid phase to obtain a product containing alkylate, wherein a suspension containing isoparaffin and a granular zeolite catalyst is supplied to the upper region of and flows downwards through a gas/liquid mass transfer column having a plurality of gas-and liquid-permeable trays, a reboiler, and a reflux condenser, an isoparaffin-olefin mixture is introduced into the column below the point where the catalyst-containing suspension is supplied, liquid accumulates in the bottom of the reactor, and a part of said liquid is passed through the reboiler where it is heated to be at least partially evaporated and returned to the mass transfer column, said at least partially evaporated liquid forming an upwardly flowing vapor comprising isoparaffin, the temperatures in the mass transfer column thereby being maintained in the range from 50 to 120° C., the vapor passing upwardly through the column countercurrent to the downward flowing suspension, whereby a mixing of the downwardly flowing suspension and the upwardly flowing vapor takes place on at least some of said gas/liquid permeable trays whereby the isoparaffin and olefin are reacted to form an alkylate, a product mixture containing alkylate is withdrawn from the bottom region of the column and an alkylate product is recovered therefrom in a separation by distillation, and excess vapor reaching the top of the column is condensed in the reflux condenser and returned to the column as a reflux.

2. The process as claimed in claim 1, wherein isoparaffin and catalyst are recovered from the separation by distillation and at least partly recirculated to the upper region of the reaction column.

3. The process as claimed in claim 1 wherein isobutane and butene are supplied to the reaction column and a product mixture containing isooctane is withdrawn.

* * * * *